US011570982B2

(12) United States Patent
Herickhoff et al.

(10) Patent No.: US 11,570,982 B2
(45) Date of Patent: Feb. 7, 2023

(54) SYSTEMS AND METHODS FOR NATURAL CRYOPROTECTANTS FOR PRESERVATION OF CELLS

(71) Applicant: Membrane Protective Technologies, Inc., Fort Collins, CO (US)

(72) Inventors: Lisa A. Herickhoff, Fort Collins, CO (US); Myles Shepherd, LaPorte, CO (US)

(73) Assignee: Membrane Protective Technologies, Inc., Fort Collins, CO (US)

( * ) Notice: Subject to any disclaimer, the term of this patent is extended or adjusted under 35 U.S.C. 154(b) by 658 days.

(21) Appl. No.: 16/339,258

(22) PCT Filed: Oct. 4, 2017

(86) PCT No.: PCT/US2017/055206
§ 371 (c)(1),
(2) Date: Apr. 3, 2019

(87) PCT Pub. No.: WO2018/067747
PCT Pub. Date: Apr. 12, 2018

(65) Prior Publication Data
US 2019/0269123 A1    Sep. 5, 2019

Related U.S. Application Data

(60) Provisional application No. 62/404,034, filed on Oct. 4, 2016.

(51) Int. Cl.
| *A01N 1/02* | (2006.01) |
| *C12N 5/073* | (2010.01) |
| *C12N 5/0735* | (2010.01) |
| *C12N 5/075* | (2010.01) |
| *C12N 5/076* | (2010.01) |
| *A61K 36/73* | (2006.01) |
| *A61K 36/185* | (2006.01) |
| *A61K 36/48* | (2006.01) |
| *A61K 36/45* | (2006.01) |
| *A61K 36/63* | (2006.01) |
| *A61K 36/87* | (2006.01) |

(52) U.S. Cl.
CPC .......... *A01N 1/0221* (2013.01); *A61K 36/185* (2013.01); *A61K 36/45* (2013.01); *A61K 36/48* (2013.01); *A61K 36/63* (2013.01); *A61K 36/73* (2013.01); *A61K 36/87* (2013.01); *C12N 5/061* (2013.01); *C12N 5/0604* (2013.01); *C12N 5/0606* (2013.01); *C12N 5/0609* (2013.01)

(58) Field of Classification Search
CPC .... A01N 1/0221; A61K 36/185; A61K 36/45; A61K 36/48; A61K 36/63; A61K 36/73; A61K 36/87; C12N 5/0604; C12N 5/0606; C12N 5/0609; C12N 5/061
See application file for complete search history.

(56) References Cited

U.S. PATENT DOCUMENTS

| 5,891,617 | A | 4/1999 | Watson et al. | |
| 6,495,532 | B1 | 12/2002 | Bathurst et al. | |
| 7,622,143 | B2 | 11/2009 | Herickhoff et al. | |
| 7,960,098 | B2 | 6/2011 | Roy et al. | |
| 8,202,558 | B2 | 6/2012 | Herickhoff et al. | |
| 8,420,307 | B2 | 4/2013 | Ostermeier | |
| 9,603,355 | B2 | 3/2017 | Matsumara et al. | |
| 2003/0051270 | A1* | 3/2003 | Kmiec | C12N 15/8213 536/23.1 |
| 2004/0053204 | A1 | 3/2004 | Morris | |
| 2008/0254439 | A1* | 10/2008 | Sarhan | A01N 1/02 435/1.3 |
| 2009/0028968 | A1* | 1/2009 | Tam | A61K 36/48 514/23 |
| 2011/0086336 | A1* | 4/2011 | Herickhoff | A61P 15/00 62/62 |
| 2015/0283076 | A1* | 10/2015 | Cipolla | A61K 45/06 424/450 |
| 2016/0120824 | A1 | 5/2016 | Shrivastava | |
| 2018/0067747 | A1 | 4/2018 | Herickhoff et al. | |
| 2019/0269123 | A1* | 9/2019 | Herickhoff | A61K 36/73 |

FOREIGN PATENT DOCUMENTS

EP    0323782 B1    8/1993

OTHER PUBLICATIONS

European Patent Application No. 17859143, first named inventor: Herickhoff. Extended European Search Report dated Jul. 13, 2020. 20 pages.
European Patent Application No. 17859143, first named inventor: Herickhoff. Partial Supplementary European Search Report dated Mar. 24, 2020. 20 pages.
Australian Patent Application No. 2017340511, first named inventor: Herickhoff. Examination Report No. 1 dated Jun. 17, 2021. 7 pages.
Elliott, Gloria D., Shangping Wang, Barry J. Fuller, Elsevier, Cryoprotectants: A review of the actions and applications of cryoprotective solutes that modulate cell recovery from ultra-low temperatures, Cryobiology 76: 74-91, vww.elsevier.com/locate/ycryo, Apr. 18, 2017, 18 pages.
Barnes, David and Gordon Sato, Methods for Growth of Cultured Cells in Serum-Free Medium, Analytical Biochemistry 102, 255-270, Oct. 17, 1979, 16 pages.
Liu, Jie, Cigdem Tanrikut, Diane L. Wright, Gloria Y. Lee, Mehmet Toner, John D. Biggers, Thomas L. Toth, Elsevier, Cryopreservation of human spermatozoa with minimal non-permeable cryoprotectant, Cryobiology 72: 162-167, www.elsevier.com/locate/ycryo, Aug. 4, 2016, 6 pages.

(Continued)

*Primary Examiner* — Blaine Lankford
(74) *Attorney, Agent, or Firm* — Santangelo Law Offices, P.C.

(57) ABSTRACT

Embodiments of the present invention provide plant-derived extracts as a replacement for traditional cryoprotectants used to freeze tissue and cells providing a method to decrease post-thaw damage as created by the cryoprotectant. For example, extracts from the genus *Hippophae* or other plant sources or compositions may be used as a cryoprotectant or may even be used to replace at least some of a traditional cryoprotectant.

9 Claims, 2 Drawing Sheets

(56) References Cited

OTHER PUBLICATIONS

Sieme, Harald, Harriëtte Oldenhof, Willem F. Wolkers, Mode of action of cryoprotectants for sperm preservation, Elsevier Animal Reproduction Science 169: 2-5, www.elsevier.com/locate/anireprosci, Feb. 3, 2016, 4 pages.
U.S. Appl. No. 62/404,034, filed Oct. 4, 2016. First Named Inventor: Herickhoff.
International Application No. PCT/US17/55206, filed Oct. 4, 2017. First Named Inventor: Herickhoff.
International Application No. PCT/US17/55206, filed Oct. 4, 2017. First Named Inventor: Herickhoff. International Search Report dated Jan. 18, 2018. 5 pages.
International Application No. PCT/US17/55206, filed Oct. 4, 2017. First Named Inventor: Herickhoff. Written Opinion of the International Searching Authority dated Jan. 18, 2018. 6 pages.
Australian Patent Application No. 2017340511, Notice of acceptance of patent application, dated May 20, 2022. 4 pages.
Australian Patent Application No. 2017340511, Examination Report No. 3, dated Apr. 19, 2022. 3 pages.
Australian Patent Application No. 2017340511, Examination Report No. 2, dated Feb. 1, 2022. 5 pages.

* cited by examiner

SYSTEMS AND METHODS FOR NATURAL CRYOPROTECTANTS FOR PRESERVATION OF CELLS

CROSS-REFERENCES TO RELATED APPLICATIONS

This is the United States National Phase of International Patent Application No. PCT/US17/55206, filed Oct. 4, 2017, which claims the benefit of and priority to U.S. Provisional Application No. 62/404,034 filed Oct. 4, 2016, both said applications and any priority case are hereby incorporated by reference herein.

TECHNICAL FIELD

The present invention relates to cryopreservation of tissues and cells and methods by which to mitigate some damages associated with cryopreservation by the substitution of various plant extracts and other moieties for previously defined cryoprotectants.

BACKGROUND

It is well understood that while cryopreservation is generally a good method for preserving cells such as gametes, germ cells, unique cell lines, stem cells, bacterial, fungal, algal cells and the like, unfortunately cryopreservation can negatively affect the integrity of the cells perhaps by causing changes to the lipid bilayer, the proteins within the lipid bilayer, or even oxidative damage to the DNA and organelles. Similarly, aggregated cellular damage can be identified as damage to tissues or organs in vitro. Such changes can be fatal to the cell. For example, in cryopreserving equine and bovine sperm cells, at least 50% of the cells are dead when the cells are thawed. Similarly, in cells such as umbilical cord blood, depending on the technique used, only 40% or less of the cells may be viable.

Cryopreserved cells may be stored at about −20° C., about −80° C. or about −196° C. (liquid nitrogen storage). The transition from about 37° C. to the extreme temperatures cause damage to the membranes including reorganization of membrane lipids, cellular swelling, and the like. For example, phosphatidyl serine, normally only found on the inner leaflet of the membrane bilayer, may be externalized to the outer leaflet of the membrane. In some membranes, such as boar sperm, the plasma membrane, a non-homogeneous entity, with respect to both structure and function, may be particularly sensitive. Interestingly, it is not only mammalian cells that are subject to cryoprotectant challenges. Fish sperm may also be friable with respect to cryopreservation and cryoprotectant use.

Past methods to protect cells from damage of cryopreservation include the use of cryoprotectants such as glycerol, DMSO, methanol, the use of certain proteins, and highly concentrated sugars, or long-chain moieties. However, past cryopreservation solutions, especially when a cryoprotectant may be added, may be far outside of a physiological osmolality and the cryopreserved cell can be damaged by the ensuing osmotic stress (e.g., water efflux) and may require rehydration upon thawing. In addition, cells may experience biochemical toxicity. The effects of toxicity may include cytoskeletal reorganization, suppression of normal metabolism and membrane composition shifts. Upon thawing, if the cell has survived the effects of the toxicity, often the components of the cell can be modified such that the cell is no longer functional. In addition, cryoprotectants may act by increasing the solute concentration inside the cell to help the cell withstand freezing or may work to decrease the effects of ice crystals inside the cell by reducing intracellular water. However, many of the accepted cryoprotectants are toxic on an organismal or even cellular level. It is imperative that biologically relevant cryoprotectants must not be toxic to the cells or tissue. In fact, in most instances the use of a cryoprotectant is a balance between beneficial and inherently detrimental effects.

Generally known are methods to combat some of the biochemical toxicity including adding cryoprotectants such as glycerol in a step-wise manner, gradually increasing the concentration and/or adding cryoprotectants at reduced (e.g., refrigerated) temperatures. An example of the attempt to balance the pros and cons of cryoprotectants may include glycerol. Glycerol may be the most commonly used cryoprotectant in reproductive cells, and indeed was an enabling additive when freezing bull sperm was first developed. However, in many species such as stallion and roosters, glycerol toxicity could impact post-thaw sperm health. In addition, glycerol is a contraceptive for some species; therefore, there is a need for alternatives to glycerol and/or a method to decrease the amount of glycerol required.

In another example, cryopreservation of stem cells requires either the use of cryoprotectants that are compatible with recipient tissues (e.g., biologically inert or even non-irritating), or requires the cells to be washed prior to use. The latter, further exacerbates the damages created during cryopreservation but is the current standard. Therefore, the development of a cryoprotectant that does not require removal, and provides non-irritating functionality, is desirable.

A variety of cryoprotective agents are known to those skilled in the art. Examples of past cryoprotective agents include but are not limited to: acetamide, agaroses, alginates, alanine albumin, ammonium acetate, betaine, butanediol, chondroitin sulfate, chloroform, choline, cyclohexanediol, dextran, diethylene glycol, dimethyl acetamide, dimethyl formamide, dimethyl sulfoxide, erythritol, ethanol, ethylene glycol, monomethyl ether, ficoll, formamide, galactose, glucose, glutamine, glycerol, glycerophosphate, glycerylmonoacetate, glycine, hydroxyethyl starch, inositol, lactose, magnesium chloride, magnesium sulfate, maltose, mannitol, mannose, methanol, methoxypropanediol, methyl acetamide, methyl formamide, methyl urea, methyl glucose, methyl glycerol, milk proteins, peptones, phenol, pluronicpolyos, polyethylene glycol, polyvinylpyrrolidone, proline, propanediol, propylene glycol, pyridine N-oxide, faffinose, ribose, serine, serum proteins, sodium bromide, sodium chloride, sodium iodide, sodium nitrate, sodium nitrite, sodium sulfate, sorbitol, sucrose, trehalose, triethylene glycol, trimethylamine acetate, urea, valine and xylose. In general, these molecules can be broadly classified as alcohols, amines, sugars, starch, sugar alcohols, diol alcohols, polysaccharide, salts, solvents, polymers, or amino acids. These same agents may be effective in vitrification as well as in slow cool cryopreservation.

Inherent in cryopreservation is the desire for the cryopreserved materials to be viable after the material is thawed. Unfortunately, damage caused by the osmotic pressure changes induced by cryopreservatives is a major event in slow freezing cell injuries. Such injuries may be irreversible. Therefore, there is a desire to find alternative cryopreservative agents that may limit damage to the cells, yet still function to reduce intracellular ice.

Past examples include Roy et al. (U.S. Pat. No. 79,560, 098) which may require the addition of a chelating agent in addition to polyethylene glycol (a polyether compound) of two different molecular weights to freeze cells. In protecting organs, Bathurst et al. (U.S. Pat. No. 6,495,532) may teach the use of lysophosphotidic acids and a 'potentiating' component such as polyethylene glycol which may increase the effectiveness of lysophosphotidic acid. Polyethylene glycol may not be a naturally occurring biological product as it is derivative from petroleum. Liu et al (Cryobiology (2016) 72:162-167) may teach the use of a singular cryoprotectant which is a sugar for use during vitrification. Monosaccharides and disaccharides may be common cryoprotectants for use in sperm vitrification that may improve post thaw sperm health. There are various mechanisms of action for cryopreservation including penetrating or non-penetrating cryopreservatives and even ice nucleation (Sieme, Oldenhof, and Wolkers 2016). In a recent review of cryoprotectants, Elliott et al. (Elliott, Wang, and Fuller 2017) may speak to the issues associated with cryopreservative toxicity and the composition of cryopreservatives for cryopreservation and vitrification that include glycerol, ethylene glycol, propylene glycol, $Me_2SO_4$, trehelose, sucrose. Matsumura (U.S. Pat. No. 9,603,355) may teach the combination of monothioglycerol, a cryoprotectant, along with a membrane protectant and sperm cells. In this case the membrane protectant may be a proteinaceous compound.

Past attempts at alternatives to traditional cryoprotectants has been less satisfactory. Moreover, the addition of lipids to cell culture media may be known to be toxic to cultured cells because of problems with toxicity of free lipids in solution (D. Barnes and G. Sato (1980) Analytical Biochemistry 102, p 255). The use of general oils and specific lipids and sugars have been met with mixed results.

US Patent Publication No. US2011/0086336 to Herickhoff et al., and U.S. Pat. Nos. 8,202,558 and 7,622,143 both to Herickhoff et al., each hereby incorporated by reference in their entirety, discusses use of extracts from the genus *Hippophae* or other plant sources or compositions. The Herickhoff references relate to use of the genus *Hippophae* plant extracts, and others, as an antioxidant which can be used in combination with standard freezing and cooling processes for cells. For example, such plant extracts and others may be used in combination with traditional cryoprotective agents. The Herickhoff references may not relate the substitution of these typical cryoprotectants with some or even all of such plant extracts and others.

Unlike existing possible solutions, surprisingly, use of some types of plant extracts or chemical or molecular biological techniques having certain types of characteristics as a partial substitution or even a full substitution of traditional cryoprotective agents has been found to work with the freezing of tissues and cells. Embodiments of the present invention provide a method of combining functionalities of additives thereby minimizing the number of compounds that may be required for cryopreservation. For example, the addition of an antioxidant, plant lipids and plant derived sugars as a method to function, in part, as a cryoprotectant, may enable minimizing the use of detrimental or potentially toxic cryoprotectants such as glycerol or other traditional cryoprotectants. Moreover, embodiments of the present invention may enable the decrease in cryopreservative toxicity as well as the requirement to remove said cryopreservative from the cellular or tissue suspension.

DISCLOSURE OF THE INVENTION

Accordingly, the present invention includes a variety of aspects or embodiments which may be selected in different combinations to suit the needs of the user. As to the goals of this invention, it may be understood that attempts at adding cryoprotectants different from those in the past, have been fraught with hurdles including rendering the cells non-viable, biologically inactive, decreasing motility, and/or failing to confer protective benefits. In addition, some moieties can act as cryosensitizers (e.g., reducing post-thaw survival) or may require removal immediately post-thaw. A more organic solution for the cryoprotectant functionality is necessary in a market where customers are demanding 'all natural' products. The ability to add a mixture of compounds that can serve as a cryoprotectant and assist in retaining the integrity of the cell, or tissue with respect to its functionality post thaw perhaps without required removal post-thaw, is a general goal of this system.

Another goal of the invention may be to provide a cryoprotectant for freezing cells and tissues that lessens the detrimental effects that past cryoprotectants have had on cells for the freezing process. Aspects of the invention may provide exclusion of all or even substantially all of past damaging cryoprotectants. In some embodiments, the present invention may provide use of a small amount of old cryoprotectants.

Embodiments of the present invention can accomplish various goals that can be implemented either alone or in combinations to achieve a variety of objectives. In one general goal, it can function for a large variety of cells, cellular collections, mixtures of cell types, tissues, tissue samples, organs and other samples to be cryopreserved that may benefit such as from the use of replacing traditional cryopreservatives, such as glycerol, perhaps in part or even in total, with natural substances in the cryopreservation solution.

In another general objective, embodiments of the present invention may include the ability to decrease the relative discrepancy between intracellular and extracellular osmolarity or osmolality while still creating a method by which to decrease intracellular water and function as a cryoprotectant.

In another general objective, embodiments of the present technology can include the ability to reduce osmotic pressure in cells for the freezing process.

Of course, other goals and objectives of the present invention may exist and may be disclosed throughout other areas of the specification and figures. It should be understood that embodiments of the present invention may include modifications which may allowance for the different amounts of alternative cryoprotectants to be used in different applications.

BRIEF DESCRIPTION OF DRAWINGS

FIG. 3 graphically demonstrates the effects of increasing substitution of glycerol with sea buckthorn pulp oil on bull sperm motility. In this example, EYC 7 is the control method where glycerol comprises the entire cryoprotectant at 7% (final, v/v). GG 5, 6 and 7 represent glycerol at either 2.5, 3 or 3.5% (final, v/v) with Sea buckthorn pulp oil at 5% therefore the total cryopreservative concentration was 7.5, 8 or 8.5% total (final v/v) in ejaculates from 3 different bulls then frozen in one of 3 methods (fast (F), normal (N) or slow (S). Total motility and progressive motility are a measure of post-thaw sperm health.

FIG. 4 demonstrates the positive effects of replacing glycerol with Sea buckthorn pulp oil (GGP) or Sea buckthorn pulp oil (GGP) plus Sea buckthorn juice (GG1) on post-thaw sperm attributes. Live_Intact are those cells having an intact plasma membrane plus an intact (fully functional) acrosome. These cells could be used to fertilize an oocyte. Dead_reacted are those cells that have a compromised or damaged plasma membrane. Motile_percent of_total demonstrates those cells that are actively swimming or have tail propulsion. Each of these sperm health traits are shown immediately post-thaw (0 hr.) and after being held 3 hours at 37 C (3 hr.).

MODE(S) FOR CARRYING OUT THE INVENTION

As mentioned earlier, the present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. The specific embodiment or embodiments shown are examples only. The specification should be understood and is intended as supporting broad claims as well as each embodiment, and even claims where other embodiments may be excluded. Importantly, disclosure of merely exemplary embodiments is not meant to limit the breadth of other more encompassing claims that may be made where such may be only one of several methods or embodiments which could be employed in a broader claim or the like. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

Embodiments of the present invention relate to a combination of compounds that together are cryoprotectant and also protect in vitro cells, tissues or even organs from damage during cryopreservation. Various embodiments of the present invention relate to a combination of compounds that together may be antioxidant protecting in vitro cells, tissues or organs from damage during in vitro processing as well as cryopreservation. The invention relates to a combination of compounds that together are naturally occurring, but may also be manufactured synthetically to produce chemically identically compounds. The compounds in the concentration utilized may be non-toxic to the material being cryopreserved. The disclosed invention may also contain compounds that may inhibit ice crystallization. The disclosed invention may also reduce or eliminate the need for cryoprotective agents. The disclosed invention relates to the use of Sea Buckthorn extracts in combination with each other and in combination with each other, to serve as a cryoprotectant. This cryoprotectant can be added to any variety of cell or tissue types to decrease cellular water (increasing solute concentration) thereby protecting the cell or tissue during cryopreservation. The invention may include glucose, fructose, methyl cellulose or trehalose, glycerol, or any other combination of the aforementioned cryoprotectants to further modify the osmotic pressure to that required by the specific cell type or line, generally and approximately 1000 mOsm.

Embodiments of the present invention may also include the addition of the cryoprotectant can occur in either a stepwise addition or a single step as is necessary for the particular cell or tissue type. It may be understood that the invention may also be utilized for vitrification. The invention may include specialized cooling method to enable or optimize the use of an alternate cryoprotectant. The invention may be applicable to a wide variety of commonly utilized media for cryopreservation.

In one embodiment of the present invention, the technology may be applied to cells, tissues, biologic extracts, serum, or the like. In other embodiments, a new cryopreservative may be used in conjunction with a traditional cryopreservative perhaps to create a synergy between the cryopreservatives. In yet other embodiments, a new cryopreservative may be used in any of the methods commonly used to freeze cells, tissues or organs including freezing, controlled rate freezing, vitrification, ultrafast freezing, ultrafast freezing using a micro-capillary system, ultra-fast vitrification, liquidus tracking, slow programmable freezers, reprofusion, two-step (equilibrium freezing), a Mr. Frosty® Cryo freezing container and similar freezing containers or freezing racks, encapsulation, or the like. In another embodiment, a cryoprotectant does not need to be washed from a tissues or cells after freezing. In another embodiment, a cryopreservative may also act as an antioxidant and may be multi-beneficial to the cryopropreserved cells, tissues, biologic extracts, serum, or the like.

In yet other embodiments, a new cryopreservative may be used at a physiological osmotic pressure appropriate for the cell type used. The gradient between the intracellular osmotic pressure and the intracellular osmotic pressure may be decreased yet still be effective to reduce intracellular water. Moreover, in another embodiment the osmotic pressure change may be sufficient to decrease intracellular water without disrupting the plasma membrane or other membranes, organelles or tissue connections within the cell or tissue to be cryopreserved. In further embodiments, a new cryopreservative may be utilized to increase the viscosity of the media used for cryopreservation or even vitrification. Another embodiment of the present invention may include the encapsulation of said materials in a liposome or other discrete vesicle. Such enclosure may help the materials remain in suspension until such a time as they are required to be in contact with the cell, tissue, biologic extract, serum or other biological materials.

Embodiments of the present invention may provide use for Liquidus Tracking where agents may be required to have glass-forming tendencies with appropriate low viscosities and even toxicities. In such an application, it may provide incrementally increasing concentrations of penetrating cryoprotectants. Embodiments of the present invention may be utilized to create an extremely high viscosity perhaps to enable vitrification without ice nucleation and crystallization, crystal growth. A resulting product may allow achievement of a 'glassy-state' at extremely low temperatures. This achievement may be the result of interfering with the kinetics of crystal growth, the formation of an ice nucleus or even the structure of the ice formation. In yet other embodiments of the present invention, the technology may be utilized in a range of temperatures, including cooling or freezing to about 17° C., about 4° C., about −20° C., about −80° C., about −196° C. or any of the myriad of temperatures in between. In addition, the temperature may extend below that of liquid nitrogen.

The present invention may provide, in some embodiments, applying technologies to a variety of sample volumes from <about 1 µl perhaps as in an electron microscope grid to perhaps many liters of sample volume such as required for organ perfusion. Other systems may include straws (ranging from about 250 µl to about 5 ml), open pulls straws, cryoloops, hemi-straws, cryotops, cryotips, quartz microcapillary, or the like. Embodiments of the present invention may be applied to not only free cells, such as sperm cells, but may also apply to those that may be functionally interconnected such as those in smooth muscle or the like. In yet another embodiment, cells tissues or organs to be cryopreserved may be isolated from prokaryotic or eukaryotic sources including mammalian sources, plant sources, fungal sources, protist, archaeabacteria, bacteria, or may be eukaryote. These cells, tissues, organs, biologic materials, may be utilized in a number of different fields including, but not limited to reproductive therapy, haemopoietic stem cell transplantation, banking of seeds, banking of oocytes or embryos, plant genetic resource banking, regenerative medicine. Each of the aforementioned can be at a variety of concentrations including a single cell in solution such as an oocyte, millions of cells per milliliter in the case of sperm cells, >about 1 million cells in the case of an organ or complex tissue, or the like.

Embodiments of the present invention may be utilized to prolong the use of cryopreserved biological material perhaps through inhibition of damage traditionally induced by traditional cryopreservation technologies.

In yet other embodiments, the present invention may provide a reduced chemical interaction with sensitive biomolecules, reduced permeation of cryoprotectant, and may even enable the use of the cryoprotectant at different temperature ranges or with different freezing rates than may have been traditionally utilized thereby limiting the damage to the cell, organ, tissue, or biological extract.

Cryopreservation or freezing may refer to a process where organelles, cells, tissues, extracellular matrix, organs or other biological constituents are preserved by cooling to a temperature where biochemical activities are slowed or ceased temporarily, in order to preserve the biochemical structure and functions when the organelles, cells, tissues, extracellular matrix, organs or other biological constituents are warmed to biochemically active temperatures. Cryopreservation may be understood to encompass a variety of temperatures for storage including any temperatures that slow or inhibit biochemical activity and may generally be in the range of 4° C. to −196° C. and may include refrigeration, cryogenic or near-freezing temperatures. Moreover, cryopreservation may encompass the various methods to achieve the reduction in temperatures including vitrification, two-step cooling, or the like. Vitrification may be a solidification of a solution at low temperature by achieving a high viscosity perhaps without ice nucleation and crystallization.

Biological material may refer to any organdies, cells, tissues, extracellular matrix, organs or other biological constituents that may be cryopreserved from a variety of sources including prokaryotic or eukaryotic sources including mammalian sources, plant sources, fungal sources, protist, archaeabacteria, bacteria, or may be eukaryote.

A cryoprotectant may be the use of an agent that lessens or even prevents the damage of cryopreserved biological materials via a variety of mechanisms and actions including preventing intracellular ice formation, desiccation or creation of a hypoosmotic solution. A cryoprotectant may be a solute which when added to cells in their medium, may allow higher post-thaw recoveries than if it were not present (Elliott et al. 2017). A cryoprotectant, cryopreservative, or cryopreservation agents may be considered equivalent terms.

Naturally occurring may refer to materials that may be derived from a biological source found in nature.

An extract may include any variation of compounds that can be isolated as a crude or refined moiety or group of moieties. For example, an ethanol extract may include the incubation of a quantity of leaves with a quantity of ethanol. The resulting solution, whether filtered or unfiltered may be termed 'extract.'

An osmotic agent may include those materials that create an osmolality greater than that internal to a cell, tissue, organ, or biologic extract which causes a hyperosmotic response. That is, causes water to efflux out of the cell. It should be understood that the invention encompasses those osmotic agents not listed, but that may be found to act as an osmotic agent and may be compatible with the material to be cryopreserved.

Tissues and cells used in embodiments of the present invention may include one or a plurality of oocytes, sperm cells, embryos, embryonic stem cells, or any other cells or cell lines. Tissues and cells may be mammalian, non-mammalian, human, non-animal perhaps obtained from any species of animal without limitation from bovine, equine, ovine, or porcine species or breed, or avian cells obtained without limitation from chickens, ducks, geese, turkeys, pheasants, and quail, or the like. Tissues and cells may also include a plurality of cells, and/or tissues from a plurality of sources such as plant cells plus mammalian sperm cells and may not be a homogeneous composition of cell or tissue types.

Extracts individually or in various combinations or as compositions prepared by molecular biology techniques or chemical synthesis techniques which contain moieties or combinations of such moieties identified within such extracts of plant origin as described herein and without limitation may include compositions which comprise any one of or any combination of: at least an amount of antioxidant activity of at least 90 micromolar Trolox equivalent per gram, an amount of fatty acids of at least 3 percent (such as palmitic acid, linoleic acid, stearic acid and mixtures thereof), or an amount of polyphenolic compounds of at least 210 mg gallic acid equivalents per 100 grams, or as otherwise specifically described herein. A composition may include tocopherols of about 60 mg/100 g or even polar lipids of about 10% to about 15%.

Embodiments of the present invention may provide a plant-derived cryoprotectant for freezing tissues and cells which includes a plant extract and perhaps also an additional osmotic agent. Examples of a plant extract may include, but is not limited to an extract produced from a plant from one or more of the following genera: *Hippophae, Vitis, Prunus, Punica, Vaccinium, Prunus, Prunus, Rubus, Euterpe, Glycine, Lycium, Carya, Rosacea, Litchi, Amelanchier, Olea*, or the like and any combination thereof. Further examples of plant extracts may include, but is not limited to, extracts from the following genera and species: *Hippophae* (such as sea buckthorn), *Vitis* (such as grape), *Prunus, Prunus Padus* (such as chokecherry or even chokeberry), *Punica* (such as pomegranate), *Vaccinium* (such as blueberries), *Prunus* (such as plum), *Prunus* (such as cherry), *Rubus* (such as raspberry or even blackberry), *Euterpe* (such as acai), *Glycine* (such as soybeans), *Lycium* (such as gogi), *Carya* (such as pecan), *Rosacea* (such as strawberry), *Litchi* (such as lychee), *Amelanchier* (such as saskatoon), *Olea* (such as Olive), or the like, and any combination thereof.

A traditional cryoprotectant may be the additional osmotic agent of which at least some of the traditional amount of cryoprotectant may be replaced with a plant extract. Examples of an additional osmotic agent may include, but is not limited to, acetamide, agaroses, alginates, alanine albumin, ammonium acetate, betaine, butanediol, chondroitin sulfate, chloroform, choline, cyclohexanediol, dextran, diethylene glycol, dimethyl acetamide, dimethyl formamide, dimethyl sulfoxide, erythritol, ethanol, ethylene glycol, monomethyl ether, ficoll, formamide, galactose, glucose, glutamine, glycerol, glycerophosphate, glycerylmonoacetate, glycine, hydroxyethyl starch, inositol, lactose, magnesium chloride, magnesium sulfate, maltose, mannitol, mannose, methanol, methoxypropanediol, methyl acetamide, methyl formamide, methyl urea, methyl glucose, methyl glycerol, milk proteins, peptones, phenol, pluronicpolyos, polyethylene glycol, polyvinylpyrrolidone, proline, propanediol, propylene glycol, pyridine N-oxide, faffinose, ribose, serine, serum proteins, sodium bromide, sodium chloride, sodium iodide, sodium nitrate, sodium nitrite, sodium sulfate, sorbitol, sucrose, trehalose, triethylene glycol, trimethylamine acetate, urea, valine, xylose, or the like.

When a plant extract may be used as a partial replacement for a traditional cryoprotectant, the combination of plant extract to additional osmotic agent may vary. For example, a percentage ratio of a plant extract to an additional osmotic agent in a cryoprotectant may include, but is not limited to about 50% plant extract to about 50% additional osmotic agent; about 55% plant extract to about 45% additional osmotic agent; about 60% plant extract to about 40% additional osmotic agent; about 65% plant extract to about 35% additional osmotic agent; about 70% plant extract to about 30% additional osmotic agent; about 75% plant extract to about 25% additional osmotic agent; about 80% plant extract to about 20% additional osmotic agent; about 85% plant extract to about 15% additional osmotic agent; about 90% plant extract to about 10% additional osmotic agent; and about 95% plant extract to about 5% additional osmotic agent. Of course, any range of percentage ratios (e.g., 0.1%-99.9%) may be used and all are included in this disclosure.

In another example, the amount of osmotic agent used in combination with a plant extract may be less than about 7% v/v in a final concentration or may even be less than about 5% v/v in a final concentration tissue or cell cryopreservation suspension. Other amounts of v/v in a final concentration may be used including, but not limited to, less than about 10%, less than about 6.5%, less than about 6%, less than about 5.5%, less than about 4.5%, less than about 4.5%, less than about 4%, less than about 3.5%, less than about 3%, less than about 2.5%, less than about 2%, less than about 1.5%, less than about 0.5%, or the like. Of course, any range of percentages may be used and all are included in this disclosure. In a traditional cryoprotectant where glycerol may have been used as the only cryoprotectant, a standard amount of glycerol may have been between about 7% and about 10% v/v in a final concentration.

Other embodiments of the present invention may provide a plant-derived cryoprotectant for freezing cells consisting of a plant extract. Examples of a plant extract may include, but is not limited to an extract produced from a plant from one or more of the following genera: *Hippophae, Vitis, Prunus, Punica, Vaccinium, Prunus, Prunus, Rubus, Euterpe, Glycine, Lycium, Carya, Rosacea, Litchi, Amelanchier, Olea*, or the like and any combination thereof. Further examples of plant extracts may include, but is not limited to, extracts from the following genera and species: *Hippophae* (such as sea buckthorn), *Vitis* (such as grape), *Prunus, Prunus Padus* (such as chokecherry or even chokeberry), *Punica* (such as pomegranate), *Vaccinium* (such as blueberries), *Prunus* (such as plum), *Prunus* (such as cherry), *Rubus* (such as raspberry or even blackberry), *Euterpe* (such as acai), *Glycine* (such as soybeans), *Lycium* (such as gogi), *Carya* (such as pecan), *Rosacea* (such as strawberry), *Litchi* (such as lychee), *Amelanchier* (such as saskatoon), *Olea* (such as Olive), or the like, and any combination thereof. A plant extract may have characteristics such as any one or more of: at least one antioxidant which provides at least 90 µmol Trolox equivalent per gram of said extract; at least one fatty acid of at least 3 percent by volume of said extract; and at least one polyphenolic compound which provides at least 210 mg gallic acid equivalents per 100 grams of said extract, or the like.

Yet other embodiments of the present invention may provide a system for freezing tissues and cells comprising: a cryoprotectant composition comprising or perhaps consisting of any one or more of: at least one antioxidant which provides at least 90 µmol (micromolar) Trolox equivalent per gram; at least one fatty acid of at least 3 percent by volume of said cryoprotectant composition; and at least one polyphenolic compound which provides at least 210 mg gallic acid equivalents per 100 grams. A cryoprotectant having one or more of these characteristics may be a plant extract, or may be chemically defined media, or the like.

In other embodiments, the present invention may provide a system for freezing tissues or cells comprising a cryoprotectant for freezing tissues or cells, wherein said cryoprotectant may be capable of creating an osmotic pressure of an environment surrounding said tissues or said cells to between about 550 and 900 mOsm (milliosmole). In other embodiments, the present invention may provide a system for freezing tissues or cells comprising a cryoprotectant for freezing tissues or cells, wherein said cryoprotectant may be capable of creating an osmotic pressure of an environment surrounding said tissues or said cells less than about 5000 mOsm (milliosmoles). Of course, other options may include less than 4500 mOsm, less than 4000 mOsm, or the like and any and all numbers may be used and all are included in this disclosure.

A typical cryopreservative may be about 4 to about 8 times the osmotic pressure of the cell. Therefore, the present invention may provide, in various embodiments, a decreased multiple required to achieve an osmotic imbalance as reduced to perhaps about 3 to about 7 times the osmotic pressure of the cell or even less than about 4 to less than about 8 times the osmotic pressure of the cell, or the like.

The present invention may provide an osmotic pressure imbalance of an environment surrounding tissues or cells between about 3 to about 7 times the osmotic pressure of the cell or may even provide an osmotic pressure imbalance of an environment surrounding said tissues or said cells between less than about 4 to less than about 8 times the osmotic pressure of the cell. It shall be understood that a hyperosmotic tolerance may be increased by use of the various embodiments presented in this application. Furthermore, the present invention may provide a method to reduce required osmotically induced volume changes by use of a novel cryoprotectant. It is understood that an osmotically induced volume change tolerances may be affected by the cell or tissue type.

Methods of embodiments of the present invention may include providing tissues or cells, creating a suspension of said tissues or cells; adding a cryoprotectant according to any one of the various embodiments discussed herein to said tissues or cells; and perhaps even freezing said tissues or cells. Another method of the present invention may provide an improved method for freezing cells and tissues comprising the steps of: providing tissues or cells; creating a suspension of said tissues or cells; creating an osmotic pressure of said suspension to between about 550 and 900 mOsm (milliosmoles) with a cryoprotectant; and perhaps even freezing said cells.

In a step of providing tissues or cells, embodiments of the present invention may include collecting tissues or cells, obtaining tissues or cells, or any other way to make tissues or cells available.

Suspensions of tissues or cells may be diluted with an extender or other components for the freezing process. Freezing of tissues or cells may include temperatures to below −4 degrees Celsius and may include slow cool cryopreservation, vitrification, or the like. Tissues or cells may include, but are not limited to, reproductive cells, sperm cells, oocytes, embryos, and embryonic stem cells.

Embodiments of the present invention may provide that after utilizing any of the various new cryoprotectants and freezing tissues or cells or the like, the tissues and cells may be thawed according to standard practices; and the thawed tissue or cells may be utilized without washing a cryoprotectant from the tissues and cells. This may provide less waste, less steps, and overall optimal efficiency to the freezing processes and may even allow recovery of a greater percentage of the cells, tissues, or the like.

Embodiments of the present invention may provide encapsulation of cryoprotectants perhaps a liposome, other discrete vesicle, or the like. Encapsulation may allow penetration of non-membrane permeable osmotic agents to tissues, cells, or the like and may even allow controlled releases of cryoprotectant such that a cell may be exposed to a continuous gradient of osmotic pressure which may then lessen trauma or damage to a cell, tissue, or the like. Various lipids or other vesicles may be used perhaps depending on the type of cells or tissues.

Example 1: Boar Sperm Study

In one experiment, a certain percentage of the total cryoprotectant in the extender media, in this case glycerol, was replaced with sea buckthorn oil. Glycerol comprised either about 25% or about 75% of the total concentration of cryoprotectant. The total concentration of cryoprotectant was about 2% final (v/v), and the percentage of Sea buckthorn was about 6% in treatment A1 or the opposite for treatment A2 in USDA Extender (prepared by combining 88 g/l lactose, 20% (v/v) hen's egg yolk 1.5% equex paste (Nova Chemical Sales Inc., Scituate, Mass.) and 80% ddH2O, pH 6.8 and osmolality of 300-320 mOsm before cryopreservative addition).

Figure 1:
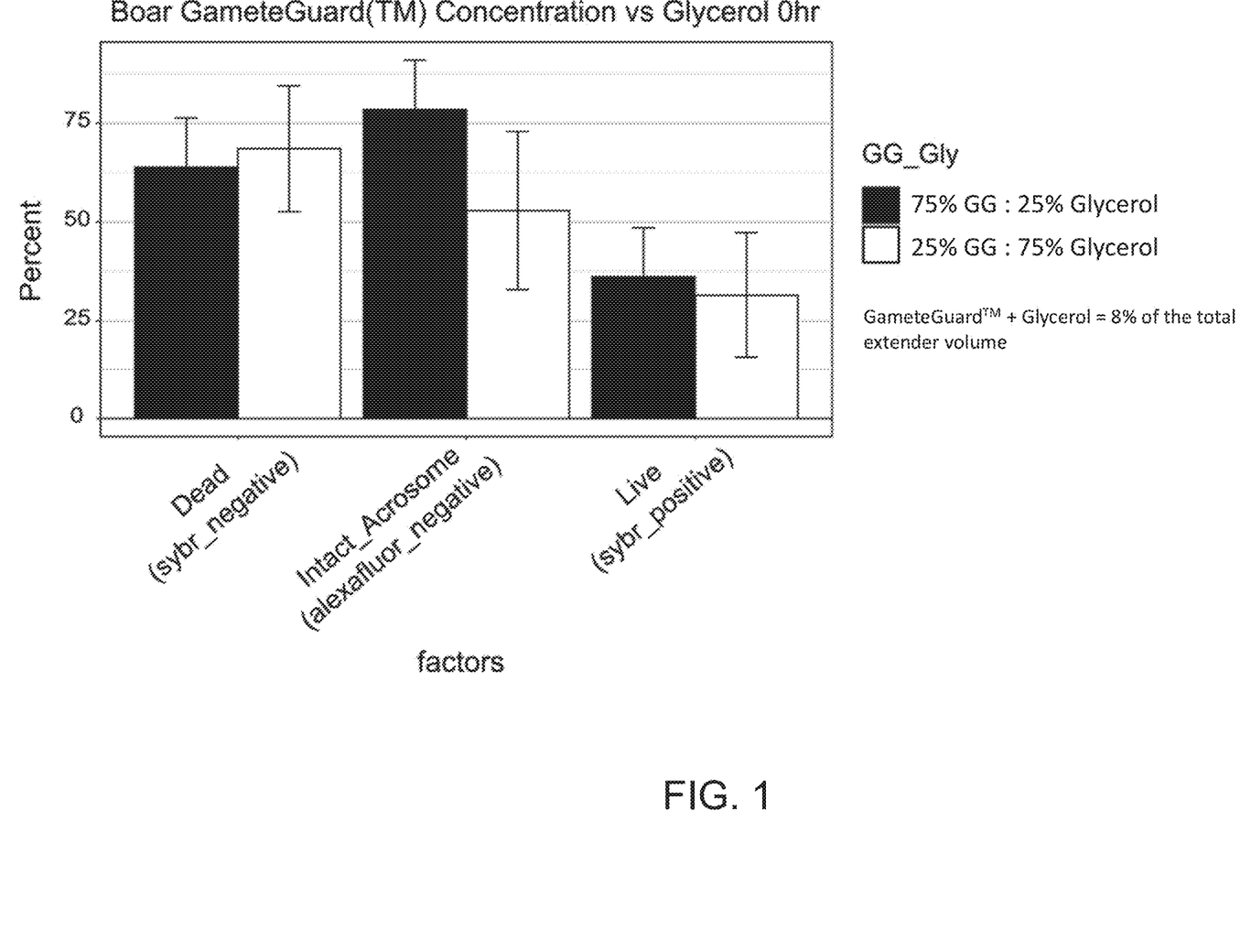
FIG. 1 shows a graph of the beneficial effects of substitution of glycerol with Sea Buckthorn pulp oil on boar sperm health immediately post-thaw (0 hour). As a measure of sperm health, the percentage of dead cells (Dead_sybr negative; unable to function post-thaw), the percentage of cells that have a fully functional acrosome (intact_acrosome_(alexafluor_negative), and the proportion of cells that have a fully intact plasma membrane (live_(sybr_positive) are shown for both a treatment where Sea Buckthorn pulp oil is substituted for the cryoprotectant, glycerol (A1) or where glycerol is the primary cyroprotectant (A2).
Figure 2:
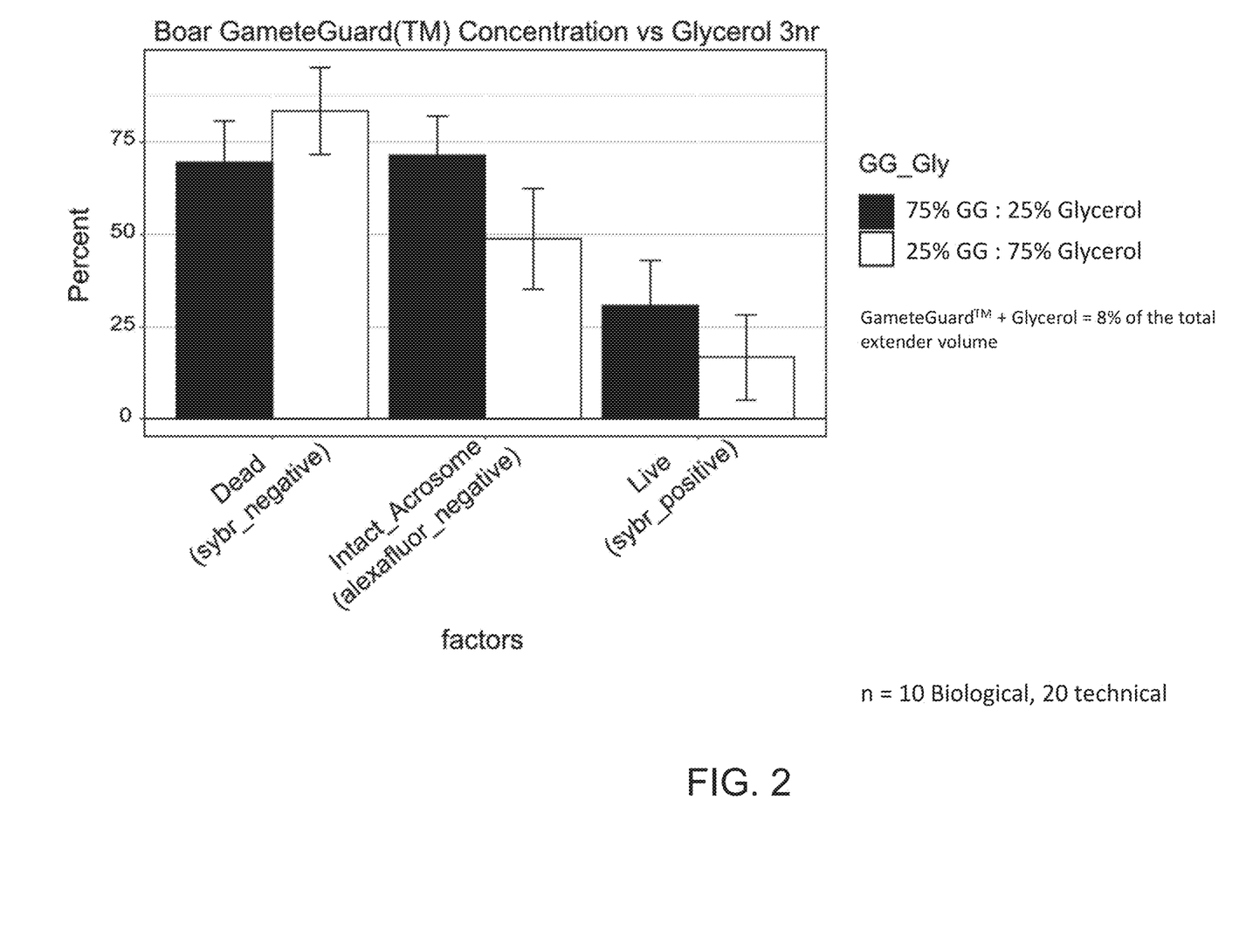
FIG. 2 shows a graph of the positive effect of substitution of glycerol with Sea Buckthorn pulp oil on boar sperm health three hours post-thaw (3 hour). As a measure of sperm health, the percentage of dead cells (Dead_(sybr negative; unable to function post-thaw), the percentage of cells that have a fully functional acrosome (intact_acrosome_(alexafluor_negative), and the proportion of cells that have a fully intact plasma membrane (live_(sybr_positive) are shown for both a treatment where Sea Buckthorn pulp oil is substituted for the cryoprotectant, glycerol or where glycerol is the cyroprotectant (A2).

An aliquot of each ejaculate was diluted to 400×106 sperm/mL in either A1 or A2 treatments. Fully extended semen were placed into cold 0.5 cc straws. Semen was frozen by placing a rack (Floating Semen Freezing Rack MOFA®#15042) containing the straws in liquid nitrogen vapor and frozen using the following curve: 4° C. to −8° C. at −20° C. per minute, −8° C. to −120° C. at −69° C. per minute, −120° C. to −140° C. at −20° C. per minute. The samples were then plunged in liquid nitrogen where they are retained for storage. Straws were thawed and semen analyzed after warming to 37° C. (0 hr.; FIG. 1) or after holding at 37 C for 3 hours (3 hr.; FIG. 2) to simulate stressful conditions.

Sperm was analyzed for acrosome intactness using FITC-PNA and membrane quality (using Sybr-green and propidium iodide). Data from this analysis is shown in FIGS. 1 and 2. In FIG. 1: Replacing ¾ of the glycerol with Sea Buckthorn (GameteGuard™ (GG); treatment A1), the percentage of sperm having intact acrosomes increased by nearly 50% and the percent sperm cells having intact membranes ('Live' on FIGS. 1 & 2) increased by about 19%. By 3 hours, this difference had increased, perhaps best illustrated by the percent of dead cells increased by about 23% in the sample containing more glycerol (FIG. 2).

TABLE 1

| Osmolality | |
| --- | --- |
| Treatment | osmolality |
| A1: 75% GG/25% glycerol | 699 |
| A2: 25% GG/75% glycerol | 902 |

As can be seen in Table 1 above, the replacement of ¾ or ¼ of the glycerol with Sea Buckthorn pulp oil decreases the osmolality. While it is creating a hyperosmotic environment, this environment may not be as extreme perhaps decreasing the damage in the cells. If the cryoprotectant was 100% glycerol, one would expect the osmolality to be greater than 1000 mOsm.

Example 2: Bull Sperm Study

In another experiment, the concentration of glycerol was varied to about 2.5%, about 3% or about 3.5% (v/v; final concentration) while the concentration of sea buckthorn oil was held constant at about 5% (v/v; final concentration. Ejaculates from three (3) bulls were utilized in this split ejaculate study. Sperm was collected using an artificial vagina, the concentration and motility determined by industry standard methods. Sperm was diluted to 80×10$^6$ sperm/ml in part A egg yolk citrate extender (without cryoprotectant, but containing 5% sea buckthorn oil) and cooled to 4° C. then part B containing either 5%, 6% or 7% glycerol. Sperm cells in each treatment were frozen using one of three methods termed: fast (F; 11 degrees C./min), normal (N; 17 degrees C./min), or slow (S; 21 degrees C./min).

Straws were analyzed after warming to 37° C. As can be seen in FIG. 3, the motility, an indicator of post-thaw sperm health, of samples containing 2.5% or 3% glycerol plus Sea Buckthorn oil (GG5 or GG6) were superior with respect to samples containing 7% glycerol with or without Sea Buckthorn (GG7). Therefore, replacing glycerol with Sea Buckthorn oil provides benefits to post-thaw sperm health regardless of the method of freezing. In all except the fast-freezing method, the sperm all the GG treatments were superior to the 7% glycerol treatment.

Example 3: Bull Sperm Study

In another experiment, the concentration of glycerol used varied between 5%, 6% or 7% (v/v; final concentration) while the concentration of sea buckthorn oil was held constant at 5% (v/v; final concentration). Ejaculates from three (3) bulls were utilized in this split ejaculate study. Sperm was collected using an artificial vagina, the concentration and motility determined by industry standard methods. Sperm was diluted to $80 \times 10^6$ sperm/ml in part A egg yolk citrate extender (without cryoprotectant, but containing 5% sea buckthorn oil) and cooled to 4° C. then part B containing either 5%, 6% or 7% glycerol. Cells were cryopreserved then thawed to assess health. Sperm cells were analyzed immediately after thawing and warming to 37° C. then they were held for 3 hours at 37° C.

Straws were analyzed after warming to 37° C. As can be seen in Table 2, 5% or 6% glycerol plus Sea Buckthorn oil (GG5 or GG6) was superior to samples containing 7% glycerol. Therefore, replacing glycerol with Sea Buckthorn oil provides benefits to sperm cells, especially during stressful conditions (compare 3 hr. 7% glycerol vs. 5% glycerol+ 5% Sea Buckthorn).

TABLE 2

| Time | Treatment | Acrosome intact, live cells | Change in cell health, from 0 to 3 hrs. |
|---|---|---|---|
| 0 Hour post thaw | 5% glycerol + 5% Sea Buckthorn | 64.75 | |
| | 7% glycerol | 64.5 | |
| 3 Hour post thaw | 5% glycerol + 5% sea buckthorn | 57.25 | −7.5 |
| | 7% glycerol | 52.5 | −12 |

Example 4: Goat Sperm

A split ejaculate study was used to assess the cryo-survival of goat sperm where glycerol is substituted in part with either Sea buckthorn pulp oil or Sea buckthorn pulp oil (GGP) plus Sea buckthorn juice (GG1). Ejaculates were collected from two goats and split into different treatments at $25 \times 10^6$ sperm/ml. Cryoprotectant was at 5% or 10% (final v/v). In this experiment a percentage of the glycerol was replaced with Sea Buckthorn oil (at 5% final v/v). Additionally, in one treatment Sea buckthorn juice was added at 3%. This experiment was conducted as a 1-step freezing. That is, sperm was diluted into the egg yolk citrate extender containing cryopreservative then cooled and frozen.

Semen was frozen by placing a rack (Floating Semen Freezing Rack MOFA®#15042) containing the straws in liquid nitrogen vapor then stored in liquid nitrogen for later analysis. Sperm health was assessed by thawing straws in a 37° C. water bath for 30-60 sec. 0 and 3 hour analysis was performed using the CASA for motility and Flow Cytometry for live/dead and acrosome integrity.

The following demonstrates a non-limiting example of the composition of the aforementioned materials used to substitute for glycerol as a cryopreservative:

| | Antioxidant (Trolox equivalent μM/g) | Polyphenolic cmpds (gallic acid equivalents; mg per 100 g raw material) | Lipid (%) |
|---|---|---|---|
| *Hippophae* pulp oil | 1290 | 216 | 80 |
| *Hippophae* juice | 2674 | 126 | 7 |
| Glycerol* | 0 | 0 | 0* |

*precursor for the synthesis of triacylglycerols and phospholipids

While the invention has been described in connection with some preferred embodiments, it is not intended to limit the scope of the invention to the particular form set forth, but on the contrary, it is intended to cover such alternatives, modifications, and equivalents as may be included within the spirit and scope of the invention as defined by the statements of inventions. Examples of alternative claims may include:

1. A plant-derived cryoprotectant for freezing tissues and cells comprising:
   a plant extract produced from a plant comprising a genus selected from a group consisting of: *Hippophae, Vitis, Prunus, Punica, Vaccinium, Prunus, Prunus, Rubus, Euterpe, Glycine, Lycium, Carya, Rosacea, Litchi, Amelanchier, Olea*, and any combination thereof; and
   an additional osmotic agent.
2. A plant-derived cryoprotectant according to clause 1 or any other clause and further comprising a percentage ratio of said plant extract to said additional osmotic agent in said plant-derived cryoprotectant selected from a group consisting of:
   about 50% plant extract to about 50% additional osmotic agent;
   about 55% plant extract to about 45% additional osmotic agent;
   about 60% plant extract to about 40% additional osmotic agent;
   about 65% plant extract to about 35% additional osmotic agent;
   about 70% plant extract to about 30% additional osmotic agent;
   about 75% plant extract to about 25% additional osmotic agent;
   about 80% plant extract to about 20% additional osmotic agent;
   about 85% plant extract to about 15% additional osmotic agent;
   about 90% plant extract to about 10% additional osmotic agent; and
   about 95% plant extract to about 5% additional osmotic agent.
3. A plant-derived cryoprotectant according to clause 1 or any other clause wherein said additional osmotic agent comprises less than about 7% v/v in a final concentration tissue or cell cryopreservation suspension.
4. A plant-derived cryoprotectant according to clause 1 or any other clause wherein said additional osmotic agent comprises glycerol.
5. A plant-derived cryoprotectant according to clause 1 or any other clause wherein said additional osmotic agent is selected from a group consisting of acetamide, agaroses, alginates, alanine albumin, ammonium acetate, betaine, butanediol, chondroitin sulfate, chloroform, choline, cyclohexanediol, dextran, diethylene glycol, dimethyl acetamide, dimethyl formamide, dimethyl sulfoxide, erythritol, ethanol, ethylene glycol, monomethyl ether, ficoll, formamide, galactose, glucose, glutamine, glycerol, glycerophosphate, glycerylmonoacetate, glycine, hydroxyethyl starch, inositol, lactose, magnesium chloride, magnesium sulfate, maltose, mannitol, mannose, methanol, methoxypropanediol, methyl acetamide, methyl formamide, methyl urea, methyl glucose, methyl glycerol, milk proteins, peptones, phenol, pluronicpolyos, polyethylene glycol, polyvinylpyrrolidone, proline, propanediol, propylene glycol, pyridine N-oxide, faffinose, ribose, serine, serum proteins, sodium bromide, sodium chloride, sodium iodide, sodium nitrate, sodium nitrite, sodium sulfate, sorbitol, sucrose, trehalose, triethylene glycol, trimethylamine acetate, urea, valine and xylose.

6. A plant-derived cryoprotectant according to clause 1 or any other clause wherein said plant extract comprises:
   at least one antioxidant which provides at least 90 μmol Trolox equivalent per gram of said extract; and
   at least one fatty acid of at least 3 percent by volume of said extract.

7. A plant-derived cryoprotectant according to clause 6 or any other clause wherein said plant extract comprises at least one polyphenolic compound which provides at least 210 mg gallic acid equivalents per 100 grams of said extract.

8. A plant-derived cryoprotectant according to clause 1 or any other clause wherein said plant-derived cryoprotectant is capable of creating an osmotic pressure of an environment surrounding said tissues or said cells to between about 550 and 900 mOsm (milliosmole).

9. An improved method for freezing cells and tissues comprising the steps of:
   providing tissues or cells;
   creating a suspension of said tissues or cells;
   adding a plant-derived cryoprotectant to said tissues or cells; and
   freezing said tissues or cells;
   wherein said plant-derived cryoprotectant comprises:
   a plant extract produced from a plant comprising a genus selected from a group consisting of: *Hippophae, Vitis, Prunus, Punica, Vaccinium, Prunus, Prunus, Rubus, Euterpe, Glycine, Lycium, Carya, Rosacea, Litchi, Amelanchier, Olea*, and any combination thereof; and
   an additional osmotic agent.

10. An improved method for freezing cells and tissues according to clause 9 or any other clause and further comprising a step of diluting said suspension of said tissues or said cells.

11. An improved method for freezing cells and tissues according to clause 9 or any other clause and further comprising a percentage ratio of said plant extract to said additional osmotic agent in said plant-derived cryoprotectant selected from a group consisting of:
   about 50% plant extract to about 50% additional osmotic agent;
   about 55% plant extract to about 45% additional osmotic agent;
   about 60% plant extract to about 40% additional osmotic agent;
   about 65% plant extract to about 35% additional osmotic agent;
   about 70% plant extract to about 30% additional osmotic agent;
   about 75% plant extract to about 25% additional osmotic agent;
   about 80% plant extract to about 20% additional osmotic agent;
   about 85% plant extract to about 15% additional osmotic agent;
   about 90% plant extract to about 10% additional osmotic agent; and
   about 95% plant extract to about 5% additional osmotic agent.

12. An improved method for freezing cells and tissues according to clause 9 or any other clause wherein said additional osmotic agent comprises less than about 7% v/v in a final concentration tissue or cell cryopreservation suspension.

13. An improved method for freezing cells and tissues according to clause 9 or any other clause wherein said additional osmotic agent comprises glycerol.

14. An improved method for freezing cells and tissues according to clause 9 or any other clause wherein said additional osmotic agent is selected from a group consisting of acetamide, agaroses, alginates, alanine albumin, ammonium acetate, betaine, butanediol, chondroitin sulfate, chloroform, choline, cyclohexanediol, dextran, diethylene glycol, dimethyl acetamide, dimethyl formamide, dimethyl sulfoxide, erythritol, ethanol, ethylene glycol, monomethyl ether, ficoll, formamide, galactose, glucose, glutamine, glycerol, glycerophosphate, glycerylmonoacetate, glycine, hydroxyethyl starch, inositol, lactose, magnesium chloride, magnesium sulfate, maltose, mannitol, mannose, methanol, methoxypropanediol, methyl acetamide, methyl formamide, methyl urea, methyl glucose, methyl glycerol, milk proteins, peptones, phenol, pluronicpolyos, polyethylene glycol, polyvinylpyrrolidone, proline, propanediol, propylene glycol, pyridine N-oxide, faffinose, ribose, serine, serum proteins, sodium bromide, sodium chloride, sodium iodide, sodium nitrate, sodium nitrite, sodium sulfate, sorbitol, sucrose, trehalose, triethylene glycol, trimethylamine acetate, urea, valine and xylose.

15. An improved method for freezing cells and tissues according to clause 9 or any other clause wherein said plant extract comprises:
   at least one antioxidant which provides at least 90 μmol Trolox equivalent per gram of said extract; and
   at least one fatty acid of at least 3 percent by volume of said extract.

16. An improved method for freezing cells and tissues according to clause 15 or any other clause wherein said plant extract comprises at least one polyphenolic compound which provides at least 210 mg gallic acid equivalents per 100 grams of said extract.

17. An improved method for freezing cells and tissues according to clause 9 or any other clause wherein said step of freezing said tissues or cells comprises a step of freezing said tissues or cells to below −4 degrees Celsius.

18. An improved method for freezing cells and tissues according to clause 9 or any other clause wherein said step of freezing said tissues or cells is selected from a group consisting of controlled rate freezing, vitrification, ultrafast freezing, ultrafast freezing using a micro-capillary system, ultra-fast vitrification, liquidus tracking, slow programmable freezers, and reprofusion, two-step.

19. An improved method for freezing cells and tissues according to clause 9 or any other clause and further comprising a step of:
   thawing said frozen tissues or cells; and
   utilizing said frozen tissue or cells without washing said cryoprotectant from said tissues and cells.

20. An improved method for freezing cells and tissues according to clause 9 or any other clause wherein said tissues or cells are selected from a group consisting of reproductive cells, sperm cells, oocytes, embryos, and embryonic stem cells.

21. An improved method for freezing cells and tissues according to clause 9 or any other clause and further comprising a step of creating an osmotic pressure of said suspension to between about 550 and 900 mOsm (milliosmole) before said step of freezing said tissues or cells.

22. A system for freezing tissues or cells comprising a cryoprotectant for freezing tissues or cells, wherein said cryoprotectant is capable of creating an osmotic pressure of an environment surrounding said tissues or said cells to between about 550 and 900 mOsm (milliosmole).

23. A system for freezing tissues and cells according to clause 22 or any other clause wherein said cryoprotectant comprises a chemically defined media.

24. A system for freezing tissues and cells according to clause 22 or any other clause wherein said cryoprotectant comprises a plant extract produced from a plant comprising a genus selected from a group consisting of: *Hippophae, Vitis, Prunus, Punica, Vaccinium, Prunus, Prunus, Rubus, Euterpe, Glycine, Lycium, Carya, Rosacea, Litchi, Amelanchier, Olea*, and any combination thereof.

25. A system for freezing tissues and cells according to clause 22 or any other clause wherein said cryoprotectant composition further comprises an additional osmotic agent.

26. A system for freezing tissues and cells according to clause 25 or any other clause and further comprising a percentage ratio of said plant extract to said additional osmotic agent in said cryoprotectant selected from a group consisting of:
   about 50% plant extract to about 50% additional osmotic agent;
   about 55% plant extract to about 45% additional osmotic agent;
   about 60% plant extract to about 40% additional osmotic agent;
   about 65% plant extract to about 35% additional osmotic agent;
   about 70% plant extract to about 30% additional osmotic agent;
   about 75% plant extract to about 25% additional osmotic agent;
   about 80% plant extract to about 20% additional osmotic agent;
   about 85% plant extract to about 15% additional osmotic agent;
   about 90% plant extract to about 10% additional osmotic agent; and
   about 95% plant extract to about 5% additional osmotic agent.

27. A system for freezing tissues and cells according to clause 25 or any other clause wherein said additional osmotic agent comprises less than about 7% v/v in a final concentration tissue or cell cryopreservation suspension.

28. A system for freezing tissues and cells according to clause 25 or any other clause wherein said additional osmotic agent comprises glycerol.

29. A system for freezing tissues and cells according to clause 25 or any other clause wherein said additional osmotic agent is selected from a group consisting of acetamide, agaroses, alginates, alanine albumin, ammonium acetate, betaine, butanediol, chondroitin sulfate, chloroform, choline, cyclohexanediol, dextran, diethylene glycol, dimethyl acetamide, dimethyl formamide, dimethyl sulfoxide, erythritol, ethanol, ethylene glycol, monomethyl ether, ficoll, formamide, galactose, glucose, glutamine, glycerol, glycerophosphate, glycerylmonoacetate, glycine, hydroxyethyl starch, inositol, lactose, magnesium chloride, magnesium sulfate, maltose, mannitol, mannose, methanol, methoxypropanediol, methyl acetamide, methyl formamide, methyl urea, methyl glucose, methyl glycerol, milk proteins, peptones, phenol, pluronicpolyos, polyethylene glycol, polyvinylpyrrolidone, proline, propanediol, propylene glycol, pyridine N-oxide, faffinose, ribose, serine, serum proteins, sodium bromide, sodium chloride, sodium iodide, sodium nitrate, sodium nitrite, sodium sulfate, sorbitol, sucrose, trehalose, triethylene glycol, trimethylamine acetate, urea, valine and xylose.

30. A system for freezing tissues and cells according to clause 24 or any other clause wherein said plant extract comprises:
   at least one antioxidant which provides at least 90 µmol Trolox equivalent per gram of said extract; and
   at least one fatty acid of at least 3 percent by volume of said extract.

31. A system for freezing tissues and cells according to clause 30 or any other clause wherein said plant extract comprises at least one polyphenolic compound which provides at least 210 mg gallic acid equivalents per 100 grams of said extract.

32. An improved method for freezing cells and tissues comprising the steps of:
   providing tissues or cells;
   creating a suspension of said tissues or cells;
   creating an osmotic pressure of said suspension to between about 550 and 900 mOsm (milliosmoles) with a cryoprotectant; and
   freezing said cells.

33. An improved method for freezing cells and tissues according to clause 32 or any other clause wherein said cryoprotectant comprises a chemically defined media.

34. An improved method for freezing cells and tissues according to clause 32 or any other clause and further comprising a step of diluting said suspension of said tissues or said cells.

35. An improved method for freezing cells and tissues according to clause 32 or any other clause wherein said cryoprotectant comprises a plant extract produced from a plant comprising a genus selected from a group consisting of: *Hippophae, Vitis, Prunus, Punica, Vaccinium, Prunus, Prunus, Rubus, Euterpe, Glycine, Lycium, Carya, Rosacea, Litchi, Amelanchier, Olea*, and any combination thereof.

36. An improved method for freezing cells and tissues according to clause 32 or any other clause wherein said cryoprotectant composition further comprises an additional osmotic agent.

37. An improved method for freezing cells and tissues according to clause 32 or any other clause and further comprising a percentage ratio of said plant extract to said additional osmotic agent in said cryoprotectant selected from a group consisting of:
   about 50% plant extract to about 50% additional osmotic agent;
   about 55% plant extract to about 45% additional osmotic agent;
   about 60% plant extract to about 40% additional osmotic agent;
   about 65% plant extract to about 35% additional osmotic agent;
   about 70% plant extract to about 30% additional osmotic agent;
   about 75% plant extract to about 25% additional osmotic agent;
   about 80% plant extract to about 20% additional osmotic agent;

about 85% plant extract to about 15% additional osmotic agent;
about 90% plant extract to about 10% additional osmotic agent; and
about 95% plant extract to about 5% additional osmotic agent.

38. An improved method for freezing cells and tissues according to clause 32 or any other clause wherein said additional osmotic agent comprises less than about 7% v/v in a final concentration tissue or cell cryopreservation suspension.

39. An improved method for freezing cells and tissues according to clause 32 or any other clause wherein said additional osmotic agent comprises glycerol.

40. An improved method for freezing cells and tissues according to clause 32 or any other clause wherein said additional osmotic agent is selected from a group consisting of acetamide, agaroses, alginates, alanine albumin, ammonium acetate, betaine, butanediol, chondroitin sulfate, chloroform, choline, cyclohexanediol, dextran, diethylene glycol, dimethyl acetamide, dimethyl formamide, dimethyl sulfoxide, erythritol, ethanol, ethylene glycol, monomethyl ether, ficoll, formamide, galactose, glucose, glutamine, glycerol, glycerophosphate, glycerylmonoacetate, glycine, hydroxyethyl starch, inositol, lactose, magnesium chloride, magnesium sulfate, maltose, mannitol, mannose, methanol, methoxypropanediol, methyl acetamide, methyl formamide, methyl urea, methyl glucose, methyl glycerol, milk proteins, peptones, phenol, pluronicpolyos, polyethylene glycol, polyvinylpyrrolidone, proline, propanediol, propylene glycol, pyridine N-oxide, faffinose, ribose, serine, serum proteins, sodium bromide, sodium chloride, sodium iodide, sodium nitrate, sodium nitrite, sodium sulfate, sorbitol, sucrose, trehalose, triethylene glycol, trimethylamine acetate, urea, valine and xylose.

41. An improved method for freezing cells and tissues according to clause 35 or any other clause wherein said plant extract comprises:
at least one antioxidant which provides at least 90 µmol Trolox equivalent per gram of said extract; and
at least one fatty acid of at least 3 percent by volume of said extract.

42. An improved method for freezing cells and tissues according to clause 41 or any other clause wherein said plant extract comprises at least one polyphenolic compound which provides at least 210 mg gallic acid equivalents per 100 grams of said extract.

43. An improved method for freezing cells and tissues according to clause 32 or any other clause wherein said step of freezing said tissues or cells comprises a step of freezing said tissues or cells to below −4 degrees Celsius.

44. An improved method for freezing cells and tissues according to clause 32 or any other clause wherein said tissues or cells are selected from a group consisting of reproductive cells, sperm cells, oocytes, embryos, and embryonic stem cells.

45. A system for freezing tissues and cells comprising:
a cryoprotectant composition comprising:
at least one antioxidant which provides at least 90 µmol (micromolar) Trolox equivalent per gram; and
at least one fatty acid of at least 3 percent by volume of said cryoprotectant composition.

46. A system for freezing tissues and cells according to clause 45 or any other clause wherein said cryoprotectant composition comprises at least one polyphenolic compound which provides at least 210 mg gallic acid equivalents per 100 grams.

47. A system for freezing tissues and cells according to clause 45 or any other clause wherein said cryoprotectant comprises a chemically defined media.

48. A system for freezing tissues and cells according to clause 45 or any other clause wherein said cryoprotectant composition comprises a plant extract produced from a plant comprising a genus selected from a group consisting of: *Hippophae, Vitis, Prunus, Punica, Vaccinium, Prunus, Prunus, Rubus, Euterpe, Glycine, Lycium, Carya, Rosacea, Litchi, Amelanchier, Olea*, and any combination thereof.

49. A system for freezing tissues and cells according to clause 45 or any other clause wherein said cryoprotectant composition further comprises an additional osmotic agent.

50. A system for freezing tissues and cells according to clause 49 or any other clause and further comprising a percentage ratio of said plant extract to said additional osmotic agent in said cryoprotectant composition selected from a group consisting of:
about 50% plant extract to about 50% additional osmotic agent;
about 55% plant extract to about 45% additional osmotic agent;
about 60% plant extract to about 40% additional osmotic agent;
about 65% plant extract to about 35% additional osmotic agent;
about 70% plant extract to about 30% additional osmotic agent;
about 75% plant extract to about 25% additional osmotic agent;
about 80% plant extract to about 20% additional osmotic agent;
about 85% plant extract to about 15% additional osmotic agent;
about 90% plant extract to about 10% additional osmotic agent; and
about 95% plant extract to about 5% additional osmotic agent.

51. A system for freezing tissues and cells according to clause 49 or any other clause wherein said additional osmotic agent comprises less than about 7% v/v in a final concentration tissue or cell cryopreservation suspension.

52. A system for freezing tissues and cells according to clause 49 or any other clause wherein said additional osmotic agent comprises glycerol.

53. A system for freezing tissues and cells according to clause 49 or any other clause wherein said additional osmotic agent is selected from a group consisting of acetamide, agaroses, alginates, alanine albumin, ammonium acetate, betaine, butanediol, chondroitin sulfate, chloroform, choline, cyclohexanediol, dextran, diethylene glycol, dimethyl acetamide, dimethyl formamide, dimethyl sulfoxide, erythritol, ethanol, ethylene glycol, monomethyl ether, ficoll, formamide, galactose, glucose, glutamine, glycerol, glycerophosphate, glycerylmonoacetate, glycine, hydroxyethyl starch, inositol, lactose, magnesium chloride, magnesium sulfate, maltose, mannitol, mannose, methanol, methoxypropanediol, methyl acetamide, methyl formamide, methyl urea, methyl glucose, methyl glycerol, milk proteins, peptones, phenol, pluronicpolyos, polyethylene glycol, polyvinylpyrrolidone, proline, propanediol, propylene glycol, pyridine N-oxide, faffinose, ribose, serine, serum proteins, sodium bromide, sodium chloride, sodium iodide, sodium nitrate, sodium nitrite, sodium sulfate, sorbitol, sucrose, trehalose, triethylene glycol, trimethylamine acetate, urea, valine and xylose.

54. A system for freezing tissues and cells according to clause 45 or any other clause wherein said cryoprotectant composition is capable of creating an osmotic pressure of an environment surrounding said tissues or said cells to between about 550 and 900 mOsm (milliosmole).

55. An improved method for freezing cells and tissues comprising the steps of:
   providing tissues or cells;
   creating a suspension of said tissues or cells;
   adding a cryoprotectant to said tissues or cells; and
   freezing said tissues or cells;
   wherein said cryoprotectant comprises:
      at least one antioxidant which provides at least 90 μmol (micromolar) Trolox equivalent per gram; and
      at least one fatty acid of at least 3 percent by volume of said cryoprotectant composition.

56. An improved method for freezing tissues and cells according to clause 55 or any other clause wherein said cryoprotectant comprises at least one polyphenolic compound which provides at least 210 mg gallic acid equivalents per 100 grams.

57. An improved method for freezing tissues and cells according to clause 55 or any other clause wherein said cryoprotectant comprises a chemically defined media.

58. An improved method for freezing cells and tissues according to clause 55 or any other clause and further comprising a step of diluting said suspension of said tissues or said cells.

59. An improved method for freezing cells and tissues according to clause 55 or any other clause wherein said cryoprotectant comprises a plant extract produced from a plant comprising a genus selected from a group consisting of: *Hippophae, Vitis, Prunus, Punica, Vaccinium, Prunus, Prunus, Rubus, Euterpe, Glycine, Lycium, Carya, Rosacea, Litchi, Amelanchier, Olea*, and any combination thereof.

60. An improved method for freezing cells and tissues according to clause 55 or any other clause wherein said cryoprotectant further comprises an additional osmotic agent.

61. An improved method for freezing cells and tissues according to clause 60 or any other clause and further comprising a percentage ratio of said plant extract to said additional osmotic agent in said cryoprotectant selected from a group consisting of:
   about 50% plant extract to about 50% additional osmotic agent;
   about 55% plant extract to about 45% additional osmotic agent;
   about 60% plant extract to about 40% additional osmotic agent;
   about 65% plant extract to about 35% additional osmotic agent;
   about 70% plant extract to about 30% additional osmotic agent;
   about 75% plant extract to about 25% additional osmotic agent;
   about 80% plant extract to about 20% additional osmotic agent;
   about 85% plant extract to about 15% additional osmotic agent;
   about 90% plant extract to about 10% additional osmotic agent; and
   about 95% plant extract to about 5% additional osmotic agent.

62. An improved method for freezing cells and tissues according to clause 60 or any other clause wherein said additional osmotic agent comprises less than about 7% v/v in a final concentration tissue or cell cryopreservation suspension.

63. An improved method for freezing cells and tissues according to clause 60 or any other clause wherein said additional osmotic agent comprises glycerol.

64. An improved method for freezing cells and tissues according to clause 60 or any other clause wherein said additional osmotic agent is selected from a group consisting of acetamide, agaroses, alginates, alanine albumin, ammonium acetate, betaine, butanediol, chondroitin sulfate, chloroform, choline, cyclohexanediol, dextran, diethylene glycol, dimethyl acetamide, dimethyl formamide, dimethyl sulfoxide, erythritol, ethanol, ethylene glycol, monomethyl ether, ficoll, formamide, galactose, glucose, glutamine, glycerol, glycerophosphate, glycerylmonoacetate, glycine, hydroxyethyl starch, inositol, lactose, magnesium chloride, magnesium sulfate, maltose, mannitol, mannose, methanol, methoxypropanediol, methyl acetamide, methyl formamide, methyl urea, methyl glucose, methyl glycerol, milk proteins, peptones, phenol, pluronicpolyos, polyethylene glycol, polyvinylpyrrolidone, proline, propanediol, propylene glycol, pyridine N-oxide, faffinose, ribose, serine, serum proteins, sodium bromide, sodium chloride, sodium iodide, sodium nitrate, sodium nitrite, sodium sulfate, sorbitol, sucrose, trehalose, triethylene glycol, trimethylamine acetate, urea, valine and xylose.

65. An improved method for freezing cells and tissues according to clause 55 or any other clause wherein said step of freezing said tissues or cells comprises a step of freezing said tissues or cells to below −4 degrees Celsius.

66. An improved method for freezing cells and tissues according to clause 55 or any other clause wherein said step of freezing said tissues or cells is selected from a group consisting of controlled rate freezing, vitrification, ultrafast freezing, ultrafast freezing using a micro-capillary system, ultra-fast vitrification, liquidus tracking, slow programmable freezers, and reprofusion, two-step.

67. An improved method for freezing cells and tissues according to clause 55 or any other clause and further comprising a step of:
   thawing said frozen tissues or cells; and
   utilizing said frozen tissue or cells without washing said cryoprotectant from said tissues and cells.

68. An improved method for freezing cells and tissues according to clause 55 or any other clause wherein said tissues or cells are selected from a group consisting of reproductive cells, sperm cells, oocytes, embryos, and embryonic stem cells.

69. An improved method for freezing cells and tissues according to clause 55 or any other clause and further comprising a step of creating an osmotic pressure of said suspension to between about 550 and 900 mOsm (milliosmole) before said step of freezing said tissues or cells.

70. A plant-derived cryoprotectant for freezing cells consisting of a plant extract, said plant extract produced from a plant comprising a genus selected from a group consisting of: *Hippophae, Vitis, Prunus, Punica, Vaccinium, Prunus, Prunus, Rubus, Euterpe, Glycine, Lycium, Carya, Rosacea, Litchi, Amelanchier, Olea*, and any combination thereof;
   wherein said plant extract comprises:
      at least one antioxidant which provides at least 90 μmol Trolox equivalent per gram of said extract; and
      at least one fatty acid of at least 3 percent by volume of said extract.

71. An improved method for freezing cells comprising the steps of:
providing tissues or cells;
creating a suspension of said tissues or cells;
adding a cryoprotectant to said tissues or cells; and
freezing said tissues or cells;
wherein said cryoprotectant comprises:
at least one antioxidant which provides at least 90 μmol Trolox equivalent per gram of said extract; and
at least one fatty acid of at least 3 percent by volume of said extract.

72. An improved method for freezing cells according clause 9, 32, 55, 71 or any other clause and further comprising a step of encapsulating said cryoprotectant in at least one type of liposome.

73. An improved method for freezing cells and tissues comprising the steps of:
providing tissues or cells;
creating a suspension of said tissues or cells;
creating an osmotic pressure of said suspension to less than about 5000 mOsm (milliosmoles) with a cryoprotectant; and
freezing said cells.

74. A system for freezing tissues and cells according to clause 45 or any other clause wherein said cryoprotectant composition is capable of creating an osmotic pressure of an environment surrounding said tissues or said cells to less than about 5000 mOsm (milliosmoles).

75. An improved method for freezing cells and tissues comprising the steps of:
providing tissues or cells;
creating a suspension of said tissues or cells;
providing an osmotic pressure imbalance of said suspension between about 3 to about 7 times the osmotic pressure of said tissues or cell with a cryoprotectant; and
freezing said tissues or cells.

76. An improved method for freezing cells and tissues comprising the steps of:
providing tissues or cells;
creating a suspension of said tissues or cells;
providing an osmotic pressure imbalance of said suspension between less than about 4 to less than about 8 times the osmotic pressure of said tissues or cells with a cryoprotectant; and
freezing said tissues or cells.

77. A system for freezing tissues or cells comprising a cryoprotectant for freezing tissues or cells, wherein said cryoprotectant is capable of creating an osmotic pressure of an environment surrounding said tissues or said cells to less than about 5000 mOsm (milliosmoles).

78. A system for freezing tissues or cells comprising a cryoprotectant for freezing tissues or cells, wherein said cryoprotectant is capable of creating an osmotic pressure imbalance of an environment surrounding said tissues or said cells between about 3 to about 7 times the osmotic pressure of the cell.

79. A system for freezing tissues or cells comprising a cryoprotectant for freezing tissues or cells, wherein said cryoprotectant is capable of creating an osmotic pressure imbalance of an environment surrounding said tissues or said cells between less than about 4 to less than about 8 times the osmotic pressure of the cell.

As can be easily understood from the foregoing, the basic concepts of the present invention may be embodied in a variety of ways. It involves both cryopreservation techniques as well as devices to accomplish the appropriate post-thaw quality of the cell. In this application, the cryoprotective techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of an "extract" should be understood to encompass disclosure of the act of "extracting"—whether explicitly discussed or not—and, conversely, were there effectively disclosure of the act of "extracting", such a disclosure should be understood to encompass disclosure of an "extract" and even a "means for extracting." Such changes and alternative terms are to be understood to be explicitly included in the description. Further, each such means (whether explicitly so described or not) should be understood as encompassing all elements that can perform the given function, and all descriptions of elements that perform a described function should be understood as a non-limiting example of means for performing that function.

Any patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in any list of references, including those listed below, or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

U.S. PATENTS

| Patent Number | Kind Code | Date Issued | Patentee |
| --- | --- | --- | --- |
| 6,495,532 | B1 | 2002 Dec. 17 | Bathurst et al. |
| 7,960,098 | B2 | 2011 Jun. 14 | Roy et al. |
| 9,603,355 | B2 | 2017 Mar. 28 | Matsumura et al. |
| 8,420,307 | B2 | 2013 Apr. 16 | Ostermeier et al. |
| 8,202,558 | B2 | 2012 Jun. 19 | Herickhoff et al. |
| 7,622,143 | B2 | 2009 Nov. 24 | Herickhoff et al. |

U.S. PUBLICATIONS

| Publication Number | Kind Code | Date Published | Patentee |
| --- | --- | --- | --- |
| 20110086336 | A1 | 2011 Apr. 14 | Herickhoff et al. |

NON-PATENT LITERATURE

ELLIOTT, Gloria D., Shangping Wang, Barry J. Fuller, ELSEVIER, Cryoprotectants: A review of the actions and applications of cryoprotective solutes that modulate cell recovery from ultra-low temperatures. Cryobiology 76: 74-91.

-continued www.elsevier.com/locate/ycryo. Apr. 18, 2017, 18 pages
BARNES, David and Gordon Sato, Methods for Growth of Cultured Cells in Serum-Free Medium, Analytical Biochemistry 102, 255-270, Oct. 17, 1979, 16 pages
LIU, Jie, Cigdem Tanrikut, Diane L. Wright, Gloria Y. Lee, Mehmet Toner, John D. Biggers, Thomas L. Toth, ELSEVIER, Cryopreservation of human spermatozoa with minimal non-permeable cryoprotectant, Cryobiology 72: 162-167, www.elsevier.com/locate/ycryo, Aug. 4. 2016, 6 pages
SIEME, Harald, Harriëtte Oldenhof, Willem F. Wolkers, Mode of action of cryoprotectants for sperm preservation, ELSEVIER Animal Reproduction Science 169: 2-5, www.elsevier.com/locate/anireprosci, Feb. 3, 2016, 4 pages Thus, the applicant(s) should be understood to have support to claim and make a statement of invention to at least: i) each of the cryoprotectant devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) an apparatus for performing the methods described herein comprising means for performing the steps, xii) the various combinations and permutations of each of the elements disclosed, xiii) each potentially dependent claim or concept as a dependency on each and every one of the independent claims or concepts presented, and xiv) all inventions described herein.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in *Hakim* v. *Cannon Avent Group, PLC,* 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. The use of the phrase, "or any other claim" is used to provide support for any claim to be dependent on any other claim, such as another dependent claim, another independent claim, a previously listed claim, a subsequently listed claim, and the like. As one clarifying example, if a claim were dependent "on claim 20 or any other claim" or the like, it could be re-drafted as dependent on claim 1, claim 15, or even claim 25 (if such were to exist) if desired and still fall with the disclosure. It should be understood that this phrase also provides support for any combination of elements in the claims and even incorporates any desired proper antecedent basis for certain claim combinations such as with combinations of method, apparatus, process, and the like claims.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. An improved method for freezing cells and tissues comprising the steps of:
   providing tissues or cells;
   providing a traditional suspension for use with said tissues or cells, said suspension comprising an extender and a traditional cryoprotectant, wherein said traditional cryoprotectant does not include a plant extract;
   substituting some of said traditional cryoprotectant with a plant extract cryoprotectant to create a new cryoprotectant, wherein said new cryoprotectant comprises a plant extract cryoprotectant and traditional cryoprotectant;
   creating a new suspension for use with said tissues or cells comprising said extender and said new cryoprotectant;
   adding said new suspension to said tissues or cells to create a final concentration tissues or cells cryopreservation suspension; and
   freezing said final concentration tissues or cells cryopreservation suspension;
   wherein said plant extract cryoprotectant comprises a plant comprising a genus or family chosen from: *Hippophae, Prunus, Punica, Euterpe, Lycium, Carya, Rosacea, Litchi, Amelanchier, Olea*, and any combination thereof; and
   wherein said new cryoprotectant comprises less than about 7% v/v in said final concentration tissue or cell cryopreservation suspension, and
   further comprising a percentage ratio of said plant extract cryoprotectant to said traditional cryoprotectant in said new suspension chosen from:
   about 50% plant extract to about 50% traditional cryoprotectant;
   about 55% plant extract to about 45% traditional cryoprotectant;
   about 60% plant extract to about 40% traditional cryoprotectant;
   about 65% plant extract to about 35% traditional cryoprotectant;
   about 70% plant extract to about 30% traditional cryoprotectant;
   about 75% plant extract to about 25% traditional cryoprotectant;
   about 80% plant extract to about 20% traditional cryoprotectant;
   about 85% plant extract to about 15% traditional cryoprotectant;
   about 90% plant extract to about 10% traditional cryoprotectant; and
   about 95% plant extract to about 5% traditional cryoprotectant.

2. An improved method for freezing cells and tissues according to claim 1 wherein said traditional cryoprotectant comprises glycerol.

3. An improved method for freezing cells and tissues according to claim 1 wherein said traditional cryoprotectant is chosen from: polyols, acetamide, agaroses, alginates, alanine albumin, ammonium acetate, betaine, butanediol, chondroitin sulfate, chloroform, choline, cyclohexanediol, dextran, diethylene glycol, dimethyl acetamide, dimethyl formamide, dimethyl sulfoxide, erythritol, ethanol, ethylene glycol, monomethyl ether, ficoll, formamide, galactose, glucose, glutamine, glycerol, glycerophosphate, glycerylmonoacetate, glycine, hydroxyethyl starch, inositol, lactose, magnesium chloride, magnesium sulfate, maltose, mannitol, mannose, methanol, methoxypropanediol, methyl acetamide, methyl formamide, methyl urea, methyl glucose, methyl glycerol, milk proteins, peptones, phenol, pluronicpolyos, polyethylene glycol, polyvinylpyrrolidone, proline, propanediol, propylene glycol, pyridine N-oxide, faffinose, ribose, serine, serum proteins, sodium bromide, sodium chloride, sodium iodide, sodium nitrate, sodium nitrite, sodium sulfate, sorbitol, sucrose, trehalose, triethylene glycol, trimethylamine acetate, urea, valine and xylose.

4. An improved method for freezing cells and tissues according to claim 1 wherein said step of freezing said final concentration tissues or cells cryopreservation suspension comprises a step of freezing said final concentration tissues or cells cryopreservation suspension to below −4 degrees Celsius.

5. An improved method for freezing cells and tissues according to claim 1 wherein said step of freezing said final concentration tissues or cells cryopreservation suspension is chosen from controlled rate freezing, vitrification, ultrafast freezing, ultrafast freezing using a micro-capillary system, ultra-fast vitrification, liquidus tracking, slow programmable freezers, and reprofusion, two-step.

6. An improved method for freezing cells and tissues according to claim 1 and further comprising a step of:

thawing said final concentration frozen tissues or cells cryopreservation suspension; and utilizing said frozen tissue or cells without washing said new suspension from said tissues and cells.

7. An improved method for freezing cells and tissues according to claim 1 wherein said tissues or cells are selected from a group consisting of reproductive cells, sperm cells, oocytes, embryos, and embryonic stem cells.

8. An improved method for freezing cells and tissues according to claim 1 and further comprising a step of creating an osmotic pressure of said new suspension to between about 550 and 900 mOsm (milliosmole) before said step of freezing said final concentration tissues or cells cryopreservation suspension.

9. An improved method for freezing cells according claim 1 and further comprising a step of encapsulating said final concentration tissues or cells cryopreservation suspension in at least one type of liposome.

* * * * *